(12) United States Patent
Shimizu (10) Patent No.: US 6,877,171 B2
(45) Date of Patent: Apr. 12, 2005

(54) BLOW-OFF NOZZLE TYPE BATHTUB WITH ILLUMINATION

(76) Inventor: Hideo Shimizu, 26-26, Minami-Otsuka 1-Chome, Toshima-Ku, Tokyo (JP)

(*) Notice: Subject to any disclaimer, the term of this patent is extended or adjusted under 35 U.S.C. 154(b) by 0 days.

(21) Appl. No.: 10/179,571

(22) Filed: Jun. 24, 2002

(65) Prior Publication Data

US 2003/0000010 A1 Jan. 2, 2003

(30) Foreign Application Priority Data

Jun. 29, 2001 (JP) ......................................... 2001-197752

(51) Int. Cl.[7] .............................................. A61H 33/06
(52) U.S. Cl. ......................................... 4/541.5; 4/541.1
(58) Field of Search .............................. 4/541.1–541.5, 4/584, 593–595, 525, 559, 546, 541.6, 496; 326/101, 96

(56) References Cited

U.S. PATENT DOCUMENTS

| | | | |
|---|---|---|---|
| D17,902 S | 11/1887 | Torrance | |
| 1,223,230 A | 4/1917 | Anderson | |
| 1,247,112 A | 11/1917 | Holmberg et al. | |
| 2,604,579 A | 7/1952 | Deneboudes | 240/2 |
| D192,955 S | 6/1962 | Moore | D4/4 |
| 3,585,991 A | 6/1971 | Balamuth | 128/66 |
| 3,788,306 A | 1/1974 | Eberhard | 128/66 |
| 4,142,337 A | 3/1979 | Holcomb | 52/169.7 |
| 4,364,132 A | 12/1982 | Robinson | 4/546 |
| 4,535,489 A | 8/1985 | Elkins | 4/546 |
| D286,233 S | 10/1986 | Schreiner | D6/397 |
| D288,507 S | 3/1987 | Evans | D6/384 |
| 4,672,898 A | 6/1987 | Davidson | 108/6 |
| 4,875,958 A | 10/1989 | Kurokawa | 156/108 |
| 4,901,379 A | * 2/1990 | Chalberg et al. | 4/541.5 |
| D310,311 S | 9/1990 | Bergen et al. | D6/500 |
| 4,974,808 A | 12/1990 | Ball | 248/917 |
| 5,000,665 A | * 3/1991 | Moeller | 4/541.6 |
| D323,378 S | 1/1992 | Delepine | D23/281 |
| D324,148 S | 2/1992 | Dickman | D6/511 |
| 5,122,936 A | * 6/1992 | Guthrie | 362/101 |
| 5,165,777 A | * 11/1992 | Kira | 362/96 |

(Continued)

OTHER PUBLICATIONS

U.S. Appl. No. 29/168,037, filed Sep. 24, 2002, Shimizu.
U.S. Appl. No. 29/168,056, filed Sep. 24, 2002, Shimizu.
U.S. Appl. No. 29/168,057, filed Sep. 24, 2002, Shimizu.
U.S. Appl. No. 29/168,059, filed Sep. 24, 2002, Shimizu.
U.S. Appl. No. 29/168,064, filed Sep. 24, 2002, Shimizu.
U.S. Appl. No. 29/168,067, filed Sep. 24, 2002, Shimizu.
U.S. Appl. No. 29/168,068, filed Sep. 24, 2002, Shimizu.
U.S. Appl. No. 29/168,079, filed Sep. 24, 2002, Shimizu.
U.S. Appl. No. 29/168,071, filed Sep. 24, 2002, Shimizu.
U.S. Appl. No. 10/313,797, filed Dec. 6, 2002, Shimizu.
U.S. Appl. No. 10/179,596, filed Jun. 24, 2002, Shimizu.

Primary Examiner—Tuan Nguyen
(74) Attorney, Agent, or Firm—Ladas & Parry LLP (57) ABSTRACT

A blow-off nozzle type bathtub with illumination according to the present invention comprises a cap having a plurality of nozzles for blowing off a fluid and for irradiating an illumination light in a head portion and having an inside thereof formed in a hollow shape, a fluid supply member having a distal end opening portion thereof connected to the hollow inside of the cap and a proximal end opening portion thereof connected to a fluid supply source which is subjected to a drive control, a light guide member which has an end surface of a distal end portion thereof directed to said hollow inside of said cap and an end surface of a proximal end portion thereof directed to an illumination light source which is subjected to a drive control, and a fixing member for fixing and supporting the fluid supply member and the light guide member on a bottom wall of a bathtub vessel on a plurality of nozzles which are formed in the bottom wall of the bathtub vessel as through holes.

10 Claims, 5 Drawing Sheets

U.S. PATENT DOCUMENTS

| | | | |
|---|---|---|---|
| 5,207,499 A * | 5/1993 | Vajda et al. | 4/541.3 |
| 5,217,292 A * | 6/1993 | Chalberg | 4/541.1 |
| D356,902 S | 4/1995 | Crowell | D6/406 |
| D367,708 S | 3/1996 | Lawing et al. | D24/204 |
| D373,817 S | 9/1996 | Andronico | D23/277 |
| 5,553,735 A | 9/1996 | Kimura | 220/469 |
| 5,604,940 A * | 2/1997 | Shimizu | 4/541.1 |
| D390,376 S | 2/1998 | Chang | D6/424 |
| D412,973 S | 8/1999 | Donnely | D23/277 |
| D428,713 S | 8/2000 | Arko et al. | D6/336 |
| D444,546 S | 7/2001 | Shimizu | D23/277 |
| D448,834 S | 10/2001 | Shimizu | D23/277 |
| D451,986 S | 12/2001 | Marshall et al. | D23/280.1 |
| D453,207 S | 1/2002 | Pavlopoulos | D23/277 |
| D462,113 S | 8/2002 | Marshall et al. | D23/280.1 |
| 6,510,277 B1 * | 1/2003 | Dongo | 4/546 |
| D470,579 S | 2/2003 | Foster | D23/280.1 |
| D473,634 S | 4/2003 | Foster | D23/277 |
| D473,724 S | 4/2003 | De Wit | D6/336 |
| 6,539,561 B2 | 4/2003 | Shimizu | 4/559 |
| 6,629,320 B1 * | 10/2003 | Gardenier et al. | 4/541.5 |

\* cited by examiner

BLOW-OFF NOZZLE TYPE BATHTUB WITH ILLUMINATION

CROSS-REFERENCE TO RELATED APPLICATION

This application is related to the pending U.S. application Ser. No. 10/179,596 filed on Jun. 24, 2002.

BACKGROUND OF THE INVENTION

1. Field of the Invention

The present invention relates to a blow-off nozzle type bathtub with illumination, and in more details, to a blow-off nozzle type bathtub with illumination which can enhance a mental relaxation effect by illuminating the inside of a bathtub and also can enhance a physical fatigue recovery effect by applying a blow-off fluid to hot water in the bathtub.

2. Description of the Related Art

Figure 1:
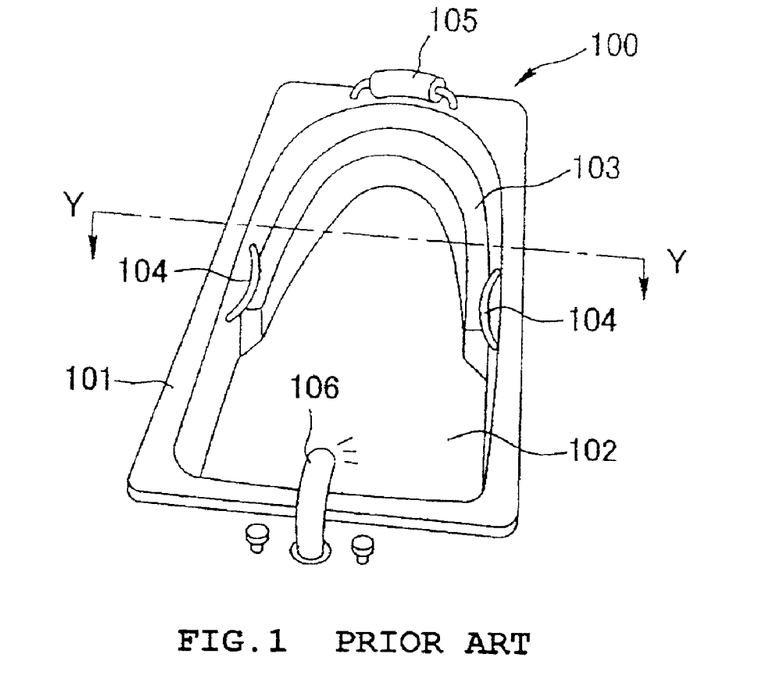
FIG. 1 is an appearance view showing a conventional general example of a bathtub device.
Figure 2:
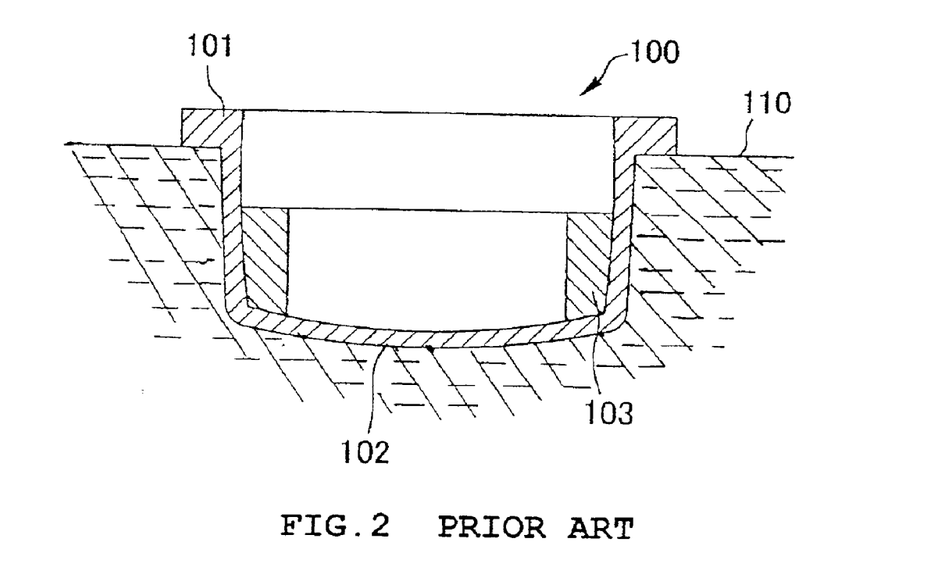
FIG. 2 is a cross-sectional view taken along a line Y—Y of FIG. 1.

As a conventional bathtub, there has been generally known a bathtub 100 which is shown in FIG. 1 as a perspective view and in FIG. 2 as a Y—Y cross-sectional view. That is, the bathtub 100 is constituted such that a rectangular bathtub container 101 is embedded into a floor surface 110, a semicircular chair portion 103 on which a bather sits is formed on a bottom surface 102 of the bathtub vessel 101, handles 104 which the bather grips are mounted on both sides of the bathtub vessel 101, and a headrest 105 made of rubber or the like with which a head portion of the bather is brought into contact is mounted on one end portion of the bathtub vessel 101. Hot water or water is supplied into the inside of the bathtub vessel 101 from a spout 106. Here, with respect to a western-style bathtub having a relatively shallow bottom, to enable a bather to take a relaxed bathing posture, there has been also known a bathtub which forms a slanted surface inclined from an upper portion to a lower portion, that is, a backrest on an inner surface of a bathtub body.

However, the bathtubs having such general structures lacks in ideas or fail to give the high-grade feeling to a bather and hence, they have been unsuccessful to give a highly effective fatigue recovery effect and a mental relaxation effect to the bather.

In view of the above, recently, there has been proposed a bathtub which is rich in ideas by directly illuminating the inside of the bathtub using a light source. That is, for example, a bathtub having an underwater illumination (so as called as "water light") having a cross section shown in FIG. 3 has been proposed. In such a bathtub 200, opening portions 204 are formed in the bathtub 200 by cutting out portions of side walls 202 or a bottom wall 203 of a bathtub vessel 201 for enabling the transmission of light, transparent members 205 such as lens are adhered to inner surfaces of opening portions 204, and light emitting members 206 such as lamps which are turned on by a switch not shown in the drawing are mounted in the opening portions 204 whereby the inside of the bathtub vessel 201 is illuminated.

Figure 3:
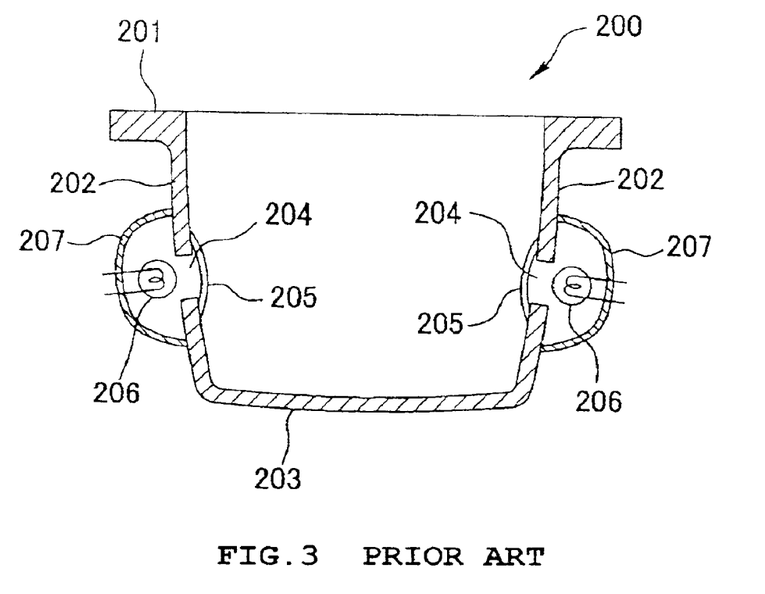
FIG. 3 is a cross-sectional view of a conventional bathtub with underwater illumination.

However, with respect to the bathtub 200 with underwater illumination which forms the opening portions 204 for transmitting light in the bathtub wall, there exists a fear that hot water or water leaks from these opening portions 204 or electricity leaks due to this leaking of water when the light emitting members 206 are formed of lamps. Accordingly, it is necessary to provide sealing members 207 on a back surface of the vessel as shown in the drawing besides mounting the transparent members 205 on an inner surface of the vessel and hence, the structure becomes complicated and pushes up a cost. Further, even when such means is provided, there still remains a possibility of leaking of water or leaking of electricity due to the fatigue generated as time lapses and hence, it is necessary to confirm the safety by always performing the maintenance and the checking. Still further, since the lamps provide the direct illumination, it gives rise to the fatigue on eyes of a bather and hence, there have been drawbacks such as the reduction of a relaxed feeling.

Figure 4:
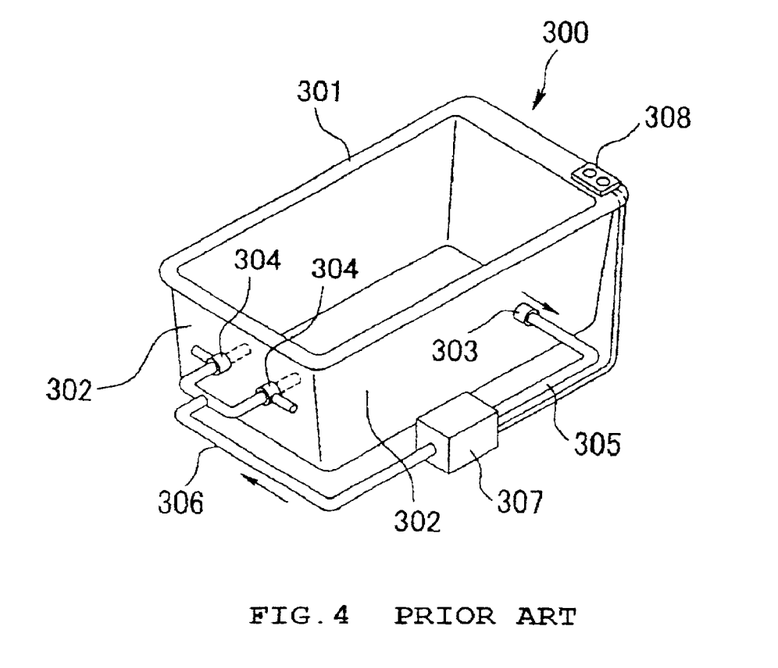
FIG. 4 is a perspective view of a conventional jet-bath type bathtub.

Further, recently, for enhancing a warming effect or a massaging effect, there has been known a jet bath (or blow-off bath) which blows off hot water mixing air bubbles therein to hot water in the inside of a bathtub or a blower bath (or air-bubble bath) which generates bubbles in hot water in the inside of a bathtub by forcedly supplying air using a blower or the like. FIG. 4 shows an example of the jet bath. As shown in the drawing, in a bathtub 300, a hot water intake portion 303 and jet discharging portions 304 are formed in a peripheral wall 302 of a bathtub vessel 301 as through holes. When a circulating pump 307 is driven by a switch 308, hot water in the inside of the bathtub vessel 310 is suck from the hot water intake portion 303 through an intake pipe 305, is supplied to the jet discharging portions 304 through a supply pipe 306, and is discharged into the inside of the bathtub vessel 301. Here, the blower bath is a bath which uses a blower, a compressor or the like in place of the circulation pump 307 and blows off air into hot water in the inside of a bathtub vessel.

The jet-bath type bathtub 300 or the blower-bath type bathtub provided with such a dedicated blow-off piping structure can surely generates an warming effect or a massaging effect so that they are effective in recovering the physical fatigue. However, it is impossible for these bathtubs to enhance a mental relaxation effect.

SUMMARY OF THE INVENTION

The present invention has been made in view of such circumstances and it is an object of the present invention to provide a blow-off nozzle type bathtub with illumination which can simultaneously satisfy a physical fatigue recovery effect and a mental relaxation effect which cannot be achieved by conventional bathtubs and can obtain a high-grade feeling.

The present invention is directed to a blow-off nozzle type bathtub with illumination and the above-mentioned object of the present invention can be achieved by mounting units each of which comprises a cap having a plurality of nozzles for blowing off a fluid and for irradiating an illumination light in a head portion thereof and having an inside thereof formed in a hollow shape, a fluid supply member having a distal end opening portion thereof connected to the hollow inside of the cap and a proximal end opening portion thereof connected to a fluid supply source which is subjected to a drive control, a light guide member which has an end surface of a distal end portion thereof directed to the hollow inside of the cap and an end surface of a proximal end portion thereof directed to an illumination light source which is subjected to a drive control, a fixing member for fixing and supporting the fluid supply member and the light guide member on a bottom wall of a bathtub vessel on a plurality of nozzles which are formed in the bottom wall of the bathtub vessel as through holes.

DETAILED DESCRIPTION OF THE PREFERRED EMBODIMENTS

Contents of the present invention are explained in detail in conjunction with attached drawings which show embodiments.

Figure 5:
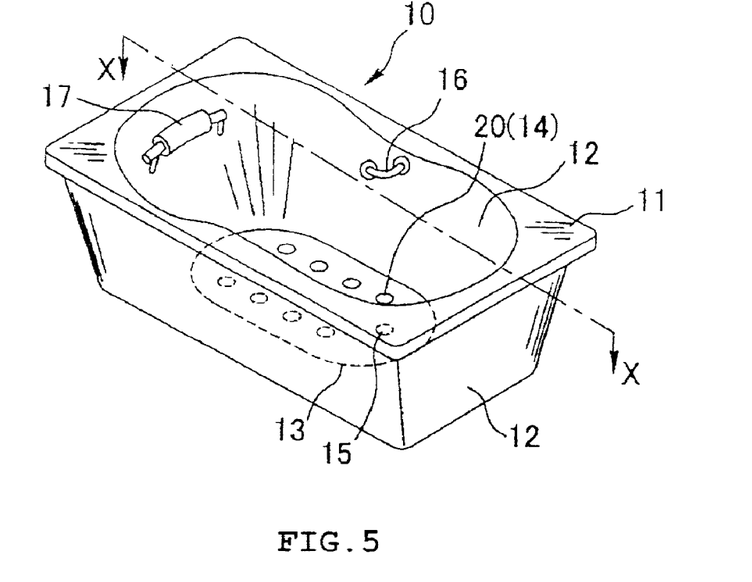
FIG. 5 is a perspective view showing one embodiment of a blow-off nozzle type bathtub with illumination according to the present invention.
Figure 6:
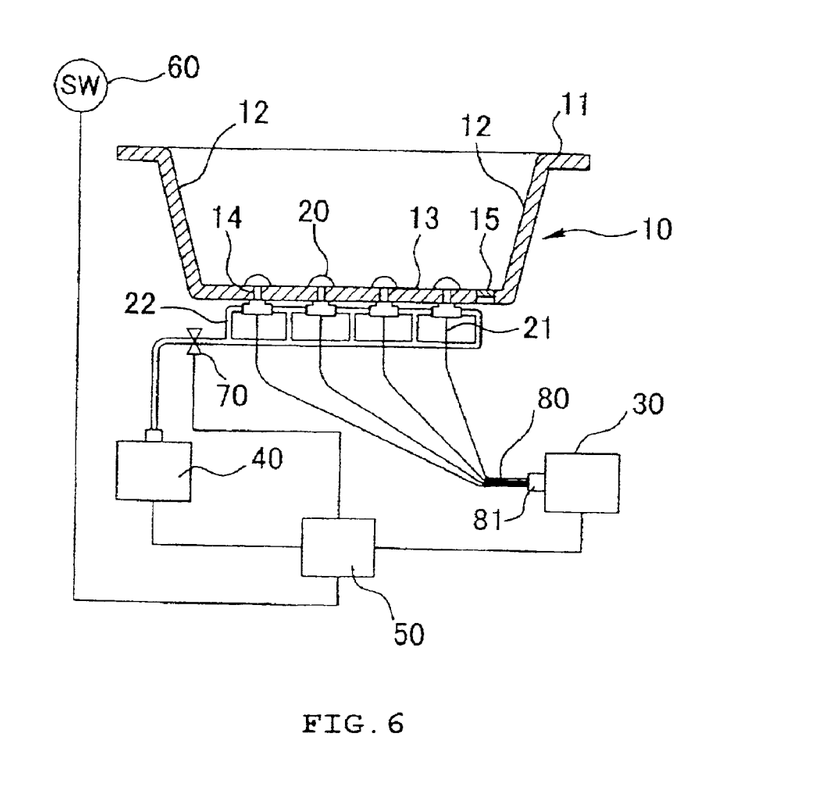
FIG. 6 is a view showing a cross section taken along a line X—X of FIG. 5 and also showing the overall constitution of the bathtub system.

FIG. 5 is a perspective view of a blow-off nozzle type bathtub with illumination (hereinafter referred to as "bathtub 10") according to one embodiment of the present invention and FIG. 6 is a view which schematically shows a cross section taken along a line X—X in FIG. 5 and a system of the bathtub 10 as a whole. In these drawings, numeral 11 indicates a bathtub vessel which is formed in a rectangular shape by molding using plastic material such as acrylic resin or methacrylic resin, for example, numeral 12 indicates a peripheral wall which is formed in a downwardly inclined manner in the inside of the bathtub vessel 11, numeral 13 indicates a bottom wall, numeral 14 indicates a plurality (in this embodiment, 2 rows×4 pieces in the longitudinal direction=8) of through holes formed in the bottom wall 13, numeral 15 indicates a drain opening, numeral 20 indicates units for blow-off fluid and illumination (hereinafter simply referred to as "unit") which are mounted in and fixed to the holes 14. As will be explained later in conjunction with FIG. 7 to FIG. 9, the unit 20 has a function of blowing off air into hot water stored in the inside of the bathtub vessel 11 as well as a function of irradiating an illumination light to the hot water stored in the inside of the bathtub vessel 11. Here, numeral 16 indicates a handle attached to the peripheral wall 12 and numeral 17 indicates a headrest. These components, however, are suitably mounted when necessary.

Further, in FIG. 6, numeral 21 indicates groups of optical fibers which are connected to a light source device 30 for illumination from the units 20, numeral 22 indicates air supply pipes which are connected from the unit 20 to a blower (air supply device) 40, numeral 50 indicates a control device which drives and controls the light source device 30 and the blower 40, numeral 60 indicates a switch which turns on or off the light source device 30 and the blower 40 through the control device 50, numeral 70 indicates a solenoid-operated valve which opens or closes the inside of the air supply pipe 22 by turning on or off the switch (the valve 70 being not always necessary although it is preferable to provide the valve 70), numeral 80 indicates a fiber cable which is constituted by binding all groups of optical fibers 21 and inserting them in a cable, and numeral 81 indicates a cable connector. Here, in this embodiment, a group of optical fibers 21 are formed by binding 28 pieces of optical fibers and 8 bundles of groups of optical fibers 21 are inserted into the fiber cable 80. Accordingly, end surfaces of 224 pieces (=28 pieces×8) of optical fibers are exposed on an proximal end portion 80a (see FIG. 10) of the fiber cable 80.

Figure 7:
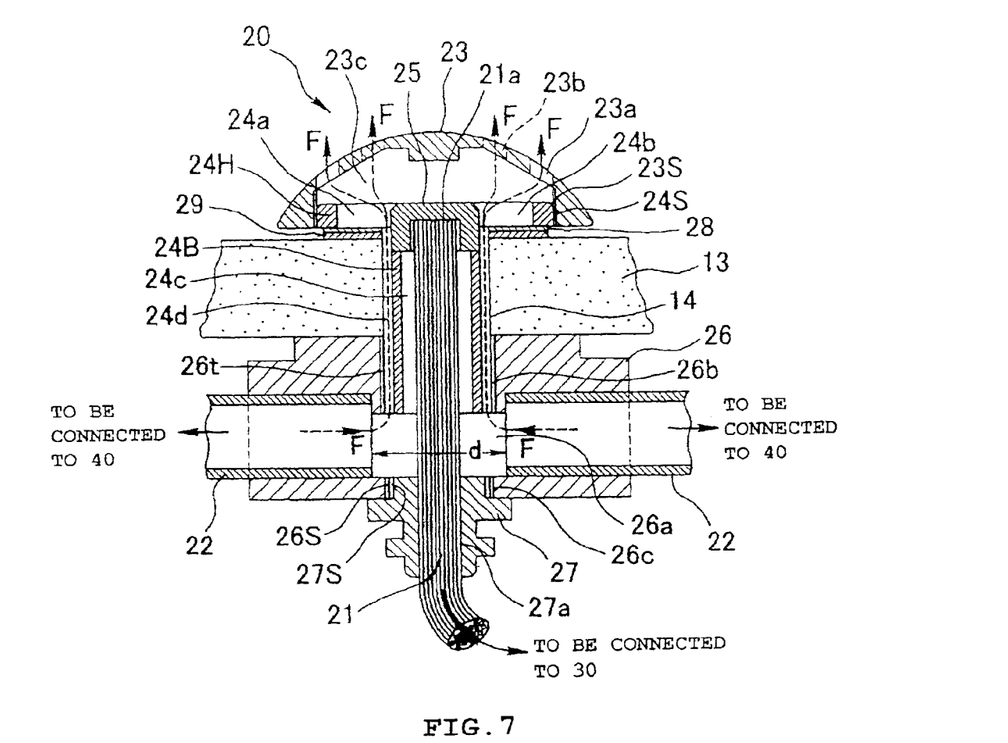
FIG. 7 is a cross-sectional view showing a unit which constitutes an essential part of the above-mentioned embodiment.
Figure 8:
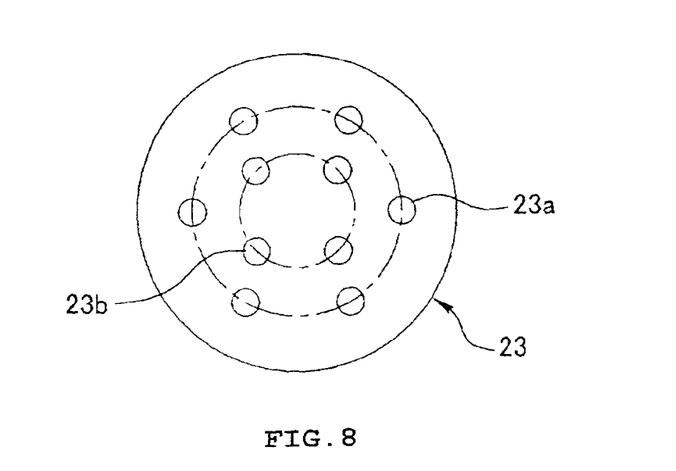
FIG. 8 is a plan view of the above-mentioned unit.

FIG. 7 is a cross-sectional view showing the detail of the unit 20. In FIG. 7, numeral 23 indicates a cap having a head portion thereof formed in a spherical shape and numerals 23a, 23b indicate a plurality (in this embodiment, 10 pieces=6 pieces at the outside+4 pieces at the inside) of nozzles for blowing off air and irradiating an illumination light which are formed in the head portion of the cap 23 as through holes having a diameter of about several mm. FIG. 8 is a plan view of the cap 23. As shown in the drawing, the nozzles 23a, 23b are arranged in a circle in an approximately equidistant manner from each other. Numeral 23c indicates a hollow portion defined by an inner wall of the cap 23 and numeral 23s indicates threads which are formed on an inner-wall profile portion of the cap 23.

Figure 9:
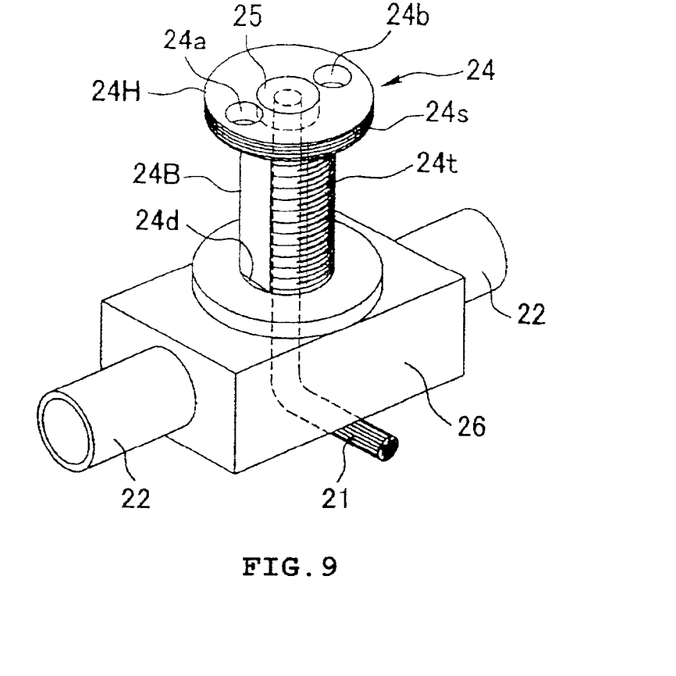
FIG. 9 is a perspective view showing the constitution of the inside when a cap of the unit is removed.

In FIG. 9 (a perspective view of the unit 20 when the above-mentioned cap 23 shown in FIG. 7 and FIG. 8 is removed), numeral 24 indicates a body formed of a metal member which has a head portion 24H thereof formed in a disc shape and a drum portion 24B formed in a shaft shape (hereinafter referred to as "body"), numeral 24a, 24b indicate air nozzles formed in the head portion 24H of the body 24 as through holes, numeral 24c indicates a cavity portion which is formed as a through hole along an axis of the drum portion 24B, numeral 24d indicates an air introduction passage by chamfering an outer peripheral surface of the drum portion 24B which is positioned below the above-mentioned air nozzles 24a, 24b into a planar surface, numeral 24s indicates threads formed on an outer peripheral surface of the head portion 24H, and numeral 24t indicates threads formed on the outer peripheral surface of the drum portion 24B except for the above-mentioned air introduction passage 24d. The threads 24s formed on the head portion 24H of the body 24 are engaged with the threads 23s formed on the inner-wall profile portion of the cap 23 so that both of them are brought into the thread engagement with each other as shown in FIG. 7.

Numeral 25 indicates a waterproof cap made of transparent acrylic resin material and is fitted on a distal end opening portion of the cavity portion 24c of the body 24 from above and has a function of covering a distal end portion 21a of the group of optical fibers 21 for ensuring the waterproofing. Here, the distal end portion 21a of the group of optical fibers 21 and the waterproof cap 25 are fixed to each other using an adhesive agent or the like.

Numeral 26 indicates a foot portion which fixes the body 24 to the bottom wall 13 of the bathtub vessel 11 and fixes and supports the group of optical fibers 21 and the air supply pipes 22 (hereinafter referred to as "foot"), numeral 26a indicates a cavity portion which is formed in a horizontal direction as a through hole in the foot 26 and has both end opening portions thereof connected with the air supply pipes 22, numeral 26b indicates an engaging hole which is formed vertically above the foot 26 as a through hole and fixes and supports the body 24, numeral 26c indicates an engaging hole which is formed vertically below the body 26 and fixes and supports the group of optical fibers 21 by way of a fiber connector 27 which will be explained later, numeral 26s indicates threads formed on the engaging hole 26c, and numeral 26t indicates threads formed on the engaging hole 26b.

As shown in FIG. 7, the air supply pipes 22 have one end portions thereof connected to the blower 40 and the other end portions thereof disposed at separated positions in the inside of the cavity portion 26a of the foot 26 with a given distance d. Further, the body 24 has the drum portion 24B thereof mounted in the hole 14 formed in the bottom wall 13 of the bathtub vessel 11 as the through hole and the threads 24t are engaged with the threads 26t of the foot 26 thus ensuring the thread mounting. Due to this thread mounting, the foot 26 is mounted on a back surface of the bottom wall 13 of the bathtub vessel 11 by way of the body 24 and the air supply pipes 22 are firmly supported on the foot 26.

Numeral 27 indicates a known fiber connector which is served for fixing and supporting the group of optical fibers 21 on the foot 26, numeral 27a indicates a cavity portion which allows the group of optical fibers 21 to pass therethrough, and numeral 27s indicates threads formed on a distal end portion of the fiber connector 27. This threads 27s are engaged with the threads 26s of the foot 26 thus ensuring the thread mounting. By inserting the fiber connector 27 into the engaging hole 26c of the foot 26 in a thread engagement after inserting the group of optical fibers 21 into the cavity portion 27a, the group of optical fibers 21 are firmly supported on the foot 26.

Numeral 28 indicates a slip washer formed of a polyester film and numeral 29 indicates a rubber-made packing. The body 24 and the foot 26 are firmly mounted on the bottom wall 13 using these parts.

By assembling the above-mentioned respective parts, the unit 20 is constituted in a manner as exactly shown in FIG. 7. The units 20 are mounted on a given number (that is, 8 pieces) of holes 14 formed in the bottom wall 13 of the bathtub vessel 11 as through holes. FIG. 5 shows a state in which all of these units 20 are mounted.

Figure 10:
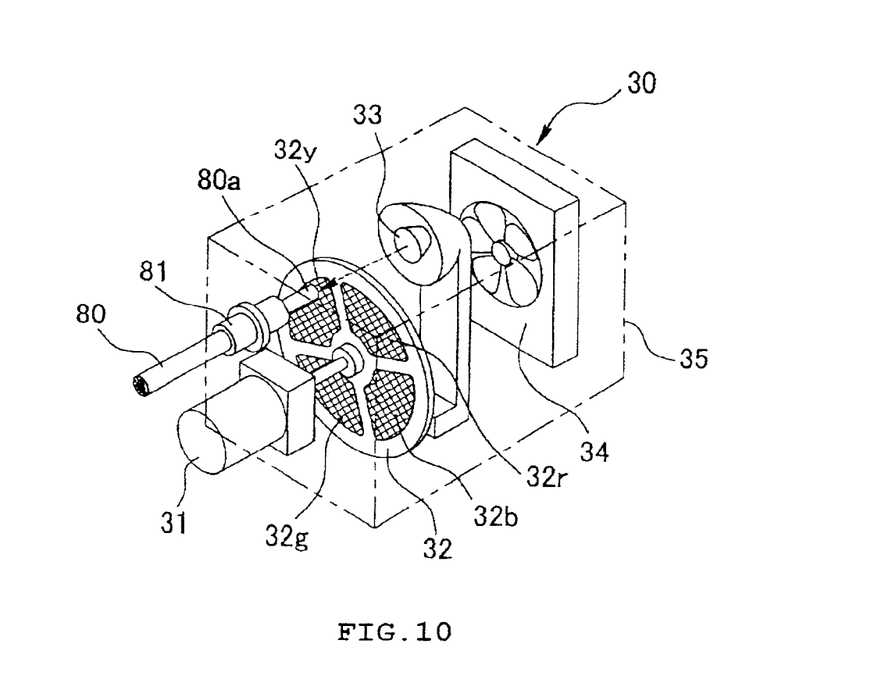
FIG. 10 is a perspective view of a light source device for illumination of the above-mentioned embodiment.

FIG. 10 is a perspective view showing the constitution of the light source device 30. In the drawing, numeral 31 indicates a motor, numeral 32 indicates a disc of color filters which is rotated by the motor 31, numerals 32r, 32b, 32g and 32y are red, blue, green and yellow color filters which are respectively laminated to the disc 32, numeral 33 indicates a halogen lamp which irradiates light to the disc 32, numeral 34 indicates a cooling fan, and numeral 35 depicted by a phantom line indicates a box which houses the above-mentioned respective parts therein. With respect to the light source device 30 having such a constitution, the proximal end portion 80a of the fiber cable 80 which is constituted by binding the whole of the group of optical fibers 21 and by accommodating them in the cable as mentioned previously is fixed to the box 35 by the cable connector 81, wherein a proximal end surface of the fiber cable 80 is disposed at a position which allows the fiber cable 80 to receive light irradiated from the halogen lamp 33 shown by an arrow by way of the disc 32.

Since the bathtub 10 is constituted in the above-mentioned manner, when hot water is stored in the bathtub vessel 11 and the switch 60 which is disposed in the inside of a bathroom is turned on, by way of the control device 50, the halogen lamp 33 of the light source device 30 emits light and, at the same time, the motor 31 is driven to rotate the color filter disc 32. Accordingly, the light which passes through respective color filters is changed sequentially (for example, in the order of red, blue, green, yellow) and is irradiated to the end surface of the proximal end portion 80a of the fiber cable 80. This light is guided to the distal end portions 21a of the group of optical fibers 21 through the group of optical fibers 21 and then is irradiated to the hot water in the inside of the bathtub vessel 11 from the hollow portion 23c of the cap 23 through the nozzles 23a, 23b. When the hot water is irradiated in this manner, the color of the hot water is changed one after the other and respective colors shine brightly so that the bather perceives a feeling as if he is bathing in the world of fantasy so that the bather can enjoy bathing with an extremely relaxed feeling. Accordingly, with the use of this bathtub 10, the mental relaxation can be enhanced.

Further, when the switch 60 is turned on, the blower 40 is driven by means of the control device 50 and, at the same time, the valve 70 is opened to forcibly supply air into the air supply pipes 22. Air forcibly supplied into the air supply pipes 22 is, as indicated by the dotted line and an arrow F, introduced into the hollow portion 23c of the cap 23 from the cavity portion 26a of the foot 26 by way of the air introduction passage 24d of the drum portion 24B of the body 24 and the air nozzles 24a, 24b of the head portion 24H of the body 24. Then, air passes through the nozzles 23a, 23b of the head portion of the cap 23 and is blown off into the hot water in the inside of the bathtub vessel 11. In this manner, when air is blown off from the bottom wall 13 of the bathtub vessel 11, bubbles rise toward a liquid level and soon extinguishes on the liquid level. Minus ions are generated due to such generation and extinction of the bubbles and the minus ions act on the bather so that an advantageous effect that the bather can activate his body is obtained. Further, along with the generation of bubbles, a liquid flow is generated in the bathtub so that the energy of this flow provides a gentle stimulus to the bather which is different from a stimulus obtained by a jet bath. Accordingly, the bather can receive the massaging effect together with the warming effect so that the circulation of blood is promoted whereby the bather can recover from the physical fatigue.

In this manner, according to the bathtub 10, the mental relaxation effect and the physical fatigue recovery effect can be simultaneously obtained and, further, it is possible to obtain an outstanding advantageous effect that the hot water shines brightly and beautifully so that a high-grade feeling is achieved.

Further, in the bathtub 10, the head portions of the caps 23 for blowing off a fluid and irradiating illumination light which are mounted on the bottom wall 13 of the bathtub vessel 11 are formed in a spherical shape. Accordingly, air blown off from the nozzles 23a, 23b and the illumination light irradiated from the nozzles 23a, 23b are spread in all directions in the inside of the bathtub so that it is possible to make the bubbles generated in the whole hot water in the inside of the bathtub and to make the illumination light shine brightly in the whole hot water in the inside of the bathtub. Further, when the caps 23 are mounted on the bottom surface 23, it is possible to prevent the bather from slipping and turning down in the inside of the bathtub.

When the bather turns off the switch 60 after bathing, the valve 70 is closed by means of the control device 50 and, at the same time, the driving of the blower 40 and the light source device 30 is stopped. When the supply of air is stopped in this manner, the hot water in the inside of the bathtub vessel 11 backflows in the air supply passage indicated by an arrow F in FIG. 7 and flows into and is stored at a level of the valve 70 provided to the air supply pipes 22.

This stored hot water is, however, returned to the inside of the bathtub vessel 11 by turning on the switch 60 again thus opening the valve 70 and, at the same time, restarting the blower 40.

Further, when all bathings in the day are completed, the residual water treatment is performed such that the drain opening 15 which is formed in the bottom wall 13 is opened so as to remove the residual hot water in the inside of the bathtub vessel 11 to the outside of the bathtub vessel 11 and, at the same time, the switch 60 is turned on so as to discharge the residual hot water remaining in the air supply passage into the bathtub vessel 11 and to discharge the residual water from the drain opening 15.

The content of the present invention has been explained in conjunction with one embodiment of the present invention. However, the present invention is not always limited to this embodiment and following various modifications can be made with resect to the constitution of the present invention.

First of all, although the above-mentioned embodiment relates to the blower-bath type bathtub which blows off air into the hot water in the inside of the bathtub, it is possible to change this bathtub to a jet-bath type bathtub which blows off hot water in place of air in a known manner using a circulation pump or the like. Here, in the jet-bath type bathtub, the stimulus given to the human body is strong and hence, it is preferable to use the blower-bath type bathtub which provides the gentle stimulus in the bathtub with illumination according to the present invention.

With respect to the shape of the head portion of the cap for blowing off a fluid and for irradiating illumination light, the shape is not limited to a spherical shape and may be a cone shape or a saddle shape. Further, it is needless to say that the number and the size of the nozzles which are formed in the head portion as through holes can be changed in a various manner when necessary.

The light source in the light source device for illumination is not limited to the halogen lamp and various kinds of lamps including an LED (Light Emitting Diode), a fluorescent lamp and the like can be used as the light source. Further, the size and the number of the optical fibers which constitute the light guide members can be arbitrarily changed depending on the necessity. Further, colors of the light source which are used for illumination can be changed into given colors by arranging kinds of color filters. Still further, the rotational speed of the disc provided with these color filters can be controlled to an arbitrary speed depending on the necessity.

As has been described heretofore, the blow-off nozzle type bathtub with illumination according to the present invention can be manufactured by the simple operation which only mounts the simple units each of which is simply constituted of the cap having a plurality of nozzles for blowing off a fluid and irradiating illumination light and members which supply a fluid to the nozzles and guide the illumination light to the nozzles on the nozzles formed in the bottom wall of the bathtub vessel as through holes. According to the bathtub which is manufactured in such a manner, the mental relaxation effect can be obtained together with the physical fatigue recovery effect and, further, it is possible to obtain a practically excellent effect that the hot water shines brightly and beautifully so that the high-grade feeling is achieved.

What is claimed is:

1. A blow-off nozzle type bathtub with illumination characterized by mounting units each of which comprises a cap having a plurality of nozzles for blowing off air and for irradiating an illumination light in a head portion thereof formed in a spherical shape and having an inside thereof formed in a hollow shape, an air supply member having a distal end opening portion thereof connected to said hollow inside of said cap and a proximal end opening portion thereof connected to an air supply source which is subjected to a drive control, a light guide member which has an end surface of a distal end portion thereof directed to said hollow inside of said cap and an end surface of a proximal end portion thereof directed to an illumination light source which is subjected to a drive control means, and a fixing member for fixing and supporting said air supply member and said light guide member on a bottom wall of a bathtub vessel on a plurality of nozzles which are formed in said bottom wall of said bathtub vessel as through holes.

2. The blow-off nozzle type bathtub with illumination according to claim 1, wherein said light guide member is formed by binding a plurality of optical fibers.

3. The blow-off nozzle type bathtub with illumination according to claim 1, wherein said light source for illumination is constituted such that said light source irradiates a plurality of colors by way of color filters which are rotated.

4. The blow-off nozzle type bathtub with illumination according to claim 2, wherein an air supply pipe is connected to said light guide member.

5. The blow-off nozzle type bathtub with illumination according to claim 4, wherein said air supply pipe is connected to a blower or an air supply device.

6. The blow-off nozzle type bathtub with illumination according to calm 5, wherein said air supply device is controlled by said drive control means.

7. The blow-off nozzle type bathtub with illumination according to claim 2, wherein a waterproof cap is fitted on a distal end opening portion of said plurality of optical fibers.

8. The blow-off nozzle type bathtub with illumination according to claim 7, wherein said waterproof cap is made of transparent material.

9. The blow-off nozzle type bathtub with illumination according to claim 3, wherein the light source is a halogen lamp and said color filters are driven by said drive control means.

10. The blow-off nozzle type bathtub with illumination according to claim 9, wherein respective rotation speeds of said color filters are controlled by said drive control means.

* * * * *